United States Patent [19]

Kathawala

[11] 4,194,002
[45] Mar. 18, 1980

[54] CHOLESTEROL ESTER-REDUCING AMIDES OF HEXAHYDROINDOLINOLS

[75] Inventor: Faizulla G. Kathawala, West Orange, N.J.

[73] Assignee: Sandoz, Inc., E. Hanover, N.J.

[21] Appl. No.: 891,298

[22] Filed: Mar. 29, 1978

[51] Int. Cl.$^2$ .................... A61K 31/40; C07D 209/04
[52] U.S. Cl. ..................... 424/274; 542/429
[58] Field of Search ............ 542/544, 545, 429; 424/274

[56] References Cited

U.S. PATENT DOCUMENTS

| | | | |
|---|---|---|---|
| 3,551,462 | 12/1970 | Seki et al. | 424/274 X |
| 3,621,043 | 11/1971 | Seki et al. | 424/274 X |
| 3,728,459 | 4/1973 | Seki et al. | 424/324 |
| 3,741,999 | 6/1973 | Seki et al. | 424/324 X |
| 3,995,059 | 11/1976 | Fukumaru et al. | 424/320 X |
| 4,129,658 | 12/1978 | Berthold | 424/274 |

Primary Examiner—Albert T. Meyers
Assistant Examiner—H. Steven Seifert
Attorney, Agent, or Firm—Gerald D. Sharkin; Richard E. Vila; Frederick H. Weinfeldt

[57] ABSTRACT

Long chain fatty acid amides of styryl hexahydroindolinols in which the amido portions have ethyleneically unsaturated positions or cyclopropanyl rings, eg 1-(1-oxo-9-cis-octadecenyl)-(3aRS, 4RS, 7aRS)-4-(Z)-(3,4-dimethoxy)-styryl-hexahydro-4-indolinol, are useful as cholesterol ester-reducing agents and are obtainable by reacting corresponding long chain carboxylic acids (or derivatives thereof) with appropriate 4-styryl-4-hexahydroindolinols.

32 Claims, No Drawings

CHOLESTEROL ESTER-REDUCING AMIDES OF HEXAHYDROINDOLINOLS

This invention relates to organic compounds and more particularly to long chain fatty acid amides of styryl hexahydroindolinols and to pharmaceutical compositions containing such compounds, as well as to the pharmaceutical use of such compounds.

The compounds of the invention are conveniently represented by the formula I:

in which R is a hexahydroindinolyl radical of the formula

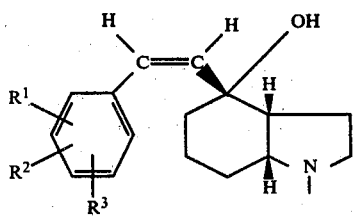

wherein $R^1$ and $R^2$ are, independently, hydrogen, fluorine, chlorine, trifluoromethyl, alkyl of 1 to 4 carbon atoms, or alkoxy of 1 to 4 carbon atoms, and $R^3$ is hydrogen, or alkoxy of 1 to 4 carbon atoms, with the proviso that when $R^1$ and $R^2$ are both other than hydrogen and $R^3$ is alkoxy then at least one of $R^1$ and $R^2$ is alkoxy, or $R^1$ and $R^2$ are bound to adjacent ring carbon atoms and are together —(CH$_2$)$_q$—, wherein q is 3 or 4, —CH=CH—CH=CH—, or —O—CH$_2$—X—, wherein X is —O— or —CH$_2$—, and $R^3$ is hydrogen, fluorine, chlorine, trifluoromethyl, alkyl of 1 to 4 carbon atoms, or alkoxy of 1 to 4 carbon atoms, and A is either of type A' which is the residue of an unsaturated long-chain fatty acid, or of type A" which is the residue of a saturated long-chain fatty acid bearing from 1 to 4 cyclopropanyl groups, (said residues being minus the carboxylic portion of the parent fatty acid). Hence compounds I=I' when A=A', and I" when A=A".

In the radical R, the phenyl ring and the 4-indolinyl nucleus are cis to each other. When $R^1$ and $R^2$ are together —CH=CH—CH=CH—, it is to be appreciated that the phenyl ring becomes a naphthyl nucleus.

Any alkyl or alkoxy radical has preferably 1 or 2 carbon atoms, especially 1 carbon atom. When $R^1$ and $R^2$ are together —(CH$_2$)$_q$—, —CH=CH—CH=CH— or —O—CH$_2$—X—, $R_3$ is preferably hydrogen.

When $R^1$ and $R^2$ are fluorine, chlorine or alkyl, these are preferably identical. When there are two or three alkoxy groups present these are preferably identical. When both of $R^1$ and $R^2$ are trifluoromethyl, these are preferably bound to non-adjacent ring carbon atoms and more preferably are at positions meta to each other and particular meta to the exocyclic double bond.

The moiety A' may be visualized as being furnished by long-chain, ethylenically unsaturated fatty acids said acids having from 8 to 24 carbon atoms and having from 1 to 4 of such unsaturated positions, and hence A' itself is an ethylenically unsaturated linear hydrocarbon chain having from 7 to 23 carbon atoms.

The moiety A" may be visualized as being furnished by linear saturated fatty acids having from 8 to 24 carbon atoms and having from 1 to 4 pairs of adjacent carbon atoms joined additionally by a methylene bridge so as to form from 1 to 4 cyclopropanyl units. Hence, the moiety A" is a saturated linear hydrocarbon chain interrupted by from 1 to 4 cyclopropanyl groups of the formula

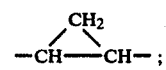

said A" having a total of from 8 to 27 carbon atoms comprising from 7 to 23 carbon atoms in the linear chain plus one carbon for each cyclopropanyl unit. A can be branched or unbranched, but is preferably unbranched.

Compounds I may be obtained by known acylation techniques (process a) of an appropriate hexahydroindolinol of formula II:

$$R-H \qquad (II)$$

in which R is as defined above, with a suitable long-chain fatty acid (or derivative thereof) corresponding to the moiety -A as defined above. Such "acylation" may be carried out by means conventionally employed in converting an amine function to its corresponding amide, such as are reported in the literature.

The acylation (process a) may conveniently be carried out by a mixed anhydride technique (process a1) wherein a compound II is treated with a mixed anhydride of the formula III:

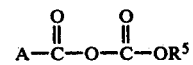

in which A is as defined above and $R^5$ is a lower unbranched alkyl having from 1 to 6 carbon atoms, at moderate temperatures, eg from about −10° C. to +35° C., in an inert organic medium, eg a chlorinated hydrocarbon, such as methylene chloride.

The mixed anhydrides (III) are obtainable by reacting (process b1) a free carboxylic acid of the formula IV:

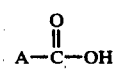

wherein A is as defined above, with a chloroformate of the formula V,

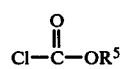

wherein $R^5$ is as defined above, in the presence of an acid acceptor, eg an organic base, such as triethylamine, at reduced temperatures, eg at from about −10° to +30° C., in an inert organic medium, eg a chlorinated hydrocarbon, such as methylene chloride.

Another convenient method of preparing compounds I comprises reacting (process a2) an acyl halide of the formula VI

in which A is as defined above, and X is either chloro- or bromo, with a compound II (as defined above), in the presence of an acid acceptor, in an inert medium at moderate temperatures, eg from about 10° to 50° C. preferably at about 20° to 30° C.

The acyl halides (VI) may be prepared in the conventional manner, eg by treating (process b2) a corresponding compound IV (as defined above), with a halogenating agent capable of contributing a chlorine or bromine atom, eg thionyl chloride (or -bromide, as appropriate).

In the above-described processes, neither the media nor the temperature are critical to the reactions, and where the reactants or reagents are liquid, an excess thereof may serve as the reaction medium. If desired a compound II may be in the form of a water-soluble acid addition salt, for example the maleate. The mixed anhydride (III) resulting from process b1) may conveniently be used in situ. That is to say that provided that the materials in the reaction mixture containing the mixed anhydride are not detrimental, they may be used directly for process a1) without recovery.

Embodiments of this invention are Compounds I' in which A' is of the formula:

   (A1):

or

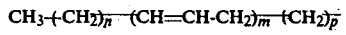   (A2);

wherein when A' is (A1) then
$f = 1$ to 10,
$g = 1$ to 4, and
$h = 3$ to 9;
particularly where $f = 5$ or 7, $g = 1$, and $h = 7$; and when A' is (A2) then
$n = 1$ to 4,
$m = 2$ to 4, and
$p = 1$ to 7;
particularly where $n = 1$ or 4, $m = $ from 2 to 4 and $p = 2$ or 6.

The total number of carbon atoms in A1 or A2 conform to the definition of A', above. That is to say that since A' is the residue of an acid having from 8 to 24 carbons; A' has from 7 to 23 carbons and from 1 to 4 unsaturated positions. Radicals A' which are unbranched are preferred. Also generally preferred are the fatty acid derivatives of the natural fatty acid order, ie those in which A' represent an odd number of carbon atoms of from 7 to 23 and accordingly A'—C≡O represent an even number of carbon atoms of from 8 to 24.

Examples of acids suitable to provide A' are given in tables I and II below:

Table I

| carbons in A'—C=O | A' = A1 | | | |
|---|---|---|---|---|
| | f | g | h | acid |
| 16 | 5 | 1 | 7 | palmitoleic |
| 18 | 7 | 1 | 7 | oleic |
| 18 | 10 | 1 | 4 | petroselenic |
| 18 | 5 | 1 | 9 | vaccenic |
| 18 | 3 | 3 | 7 | punicic (or eleostearic) |
| 18 | 1 | 4 | 7 | parinaric |

Table I-continued

| carbons in A'—C=O | A' = A1 | | | |
|---|---|---|---|---|
| | f | g | h | acid |
| 20 | 9 | 1 | 7 | gadoleic |
| 22 | 9 | 1 | 9 | cetoleic |

Table II

| carbons in A'—C=O | A' = A2 | | | |
|---|---|---|---|---|
| | n | m | p | acid |
| 18 | 4 | 2 | 6 | linoleic |
| 18 | 1 | 3 | 6 | linolenic |
| 20 | 4 | 4 | 2 | arachidonic |

Those compounds I wherein A' is derived from oleic, linoleic, linolenic, arachidonic or palmitoleic acids are particularly preferred.

It will be appreciated that the unsaturated acids which provide the moiety A' occur in isomeric forms due to the presence of the one or more unsaturated positions. The particular isomeric form of the A' moiety in a parent acid will remain the same in the resulting Compound I', since the structural configuration of the A' moiety is not changed by the processes yielding compounds I'. Compounds I' wherein the hydrogen atoms on the pair of carbons of each unsaturated position of the A'-moiety are in the cis configuration are preferred.

Particular embodiments of this invention are the compound 1-(1-oxo-9-cis-octadecenyl)-(3aRS-4RS-7aRS)-4-(Z)-(3,4-dimethoxy)-styryl-hexahydro-4-indolinol, as well as pharmaceutical compositions containing said compound as well as the use of said compound and compositions containing said compound as described herein.

When A is of type A'', then cyclopropanyl group-bearing fatty acids suitable as compounds IV, ie IV''', may be conveniently obtained by converting the unsaturated positions of corresponding long chain ethylenically unsaturated fatty acids to cyclopropanyl groups. It will be appreciated that each olefinic unit: —CH=CH— is thus replaced by a cyclopropanyl unit

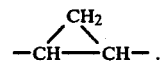

Since each cyclopropanyl unit contributes an additional carbon atom beyond the number in the linear hydrocarbon "backbone" of a radical A'', the total number of carbon atoms in A'' will equal the number of carbon atoms in the non-cyclic portion plus the total number of methylene carbon atoms of the cyclopropanyl units thereon.

For example, compounds suitable as cyclopropanyl-bearing acids (IV'') (or their derivatives) are obtainable by treatment of a corresponding mono- or poly-unsaturated long chain fatty acid (VII) with methyleneiodide ($CH_2I_2$) by the Simmons-Smith method (described in J.A.C.S. 81, 4256 (1959).

For preparing compounds IV'' bearing a single cyclopropanyl unit, the starting acids (VII) may possess either the cis-oid or trans-oid configuration. When acids with cis-oid configuration are used, the Simmons-Smith reaction, used for preparing the corresponding "cyclopropane" acids (IV"'), leads only to cis "cyclopropane" acids, and similarly the trans-acids gives the corresponding trans-"cyclopropane" acids. Mixtures will of course lead to corresponding mixture. If desired, the starting cyclopropane acid may be resolved into its antipodes, and a particular antipode then reacted with the desired optical isomer of a compound II, to give the corresponding isomeric product (I") in relatively pure isomeric form.

Similarly, for preparing cyclopropane acids (IV") bearing two or more cyclopropanyl units, the starting olefinic acids have a corresponding number of double bonds, and the Simmons-Smith reaction leads to a mixture of diastereomeric acids, which may be separated before reacting with an appropriate compound II.

Since compounds I" having only one cyclopropanyl unit have a lesser number of asymmetric carbon atoms than those derived from acid of greater unsaturation, they are generally easier to refine and are therefore, preferred from that standpoint, where ease of purification is an important factor in their preparation.

In general it is preferred that A" is unbranched. It is further preferred that each pair of hydrogen atoms bound to the tertiary carbon atoms of each cyclopropanyl group is in the cis configuration.

A preferred class of Compounds I" are those wherein A" is a cyclopropanyl-bearing hydrocarbon radical of the formula A3:

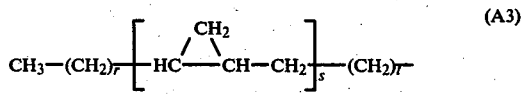

wherein r is a whole integer of from 1 to 15; s is 1 or 2; and t is a whole integer of from 1 to 13, provided that when s is 1, then r+t is from 3 to 19, and when s is 2 then r+t is from 2 to 16; and particularly those having in addition to the various preferences discussed above, one or more of the following characteristics with respect to the A"-moiety: (1) r+t=7 to 19 when s is 1; or r+t=4 to 16 when s=2; (2) r+t=an odd number when s=1, and even number when s=2; and (3) when s=1, then r=5 or 7 and t=6; and when s=2, then r=4 and t=6.

In view of the above-presented preferences it will be appreciated that it is particularly preferred that in compounds I" the A"-moiety is derived from mono- or di-unsaturated fatty acids (or esters thereof) of the type found in nature, especially palmitoleic or oleic acid (s=1); and linoleic acid (s=2).

Additional embodiments of this invention are in particular the compound 1-[1-oxo-2-cis-(octyl)-cyclopropanoctyl]-(3aRS,4RS,7aRS)-4-(Z)-(3,4-dimethoxy)-styryl-hexahydro-4-indolinol of Example 5, and pharmaceutical compositions containing said compound, as well as the use of said compound and compositions containing said compound as described herein.

PREPARATION OF COMPOUNDS II

The particular hexahydroindolinols described above as Compounds II do not form a part of this invention, as they are the invention of another, as is the following method of their preparation and intermediates thereof.

Compounds II may be obtained by a process (d) which comprises deprotecting a compound of formula II$_p$

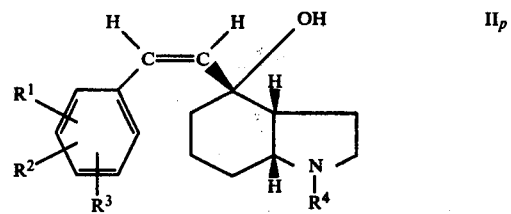

wherein
R$^1$, R$^2$ and R$^3$ are as defined above, and
R$^4$ is a protecting group.

The process may be effected in conventional manner for splitting off of amino protecting groups from similar cyclic amines, e.g. through solvolysis, especially hydrolysis. Suitable groups R$^4$ include aryloxycarbonyl, arylalkyloxycarbonyl or alkoxycarbonyl groups of up to 12 carbon atoms such as ethoxycarbonyl or methoxycarbonyl.

Preferably the reaction is effected under strongly basic conditions. A solvent system such as methanol/water or DMSO/methanol may be used. Suitable reaction temperatures may be from 50° to 250° C. The reaction may be effected in an autoclave.

Free base forms of the compounds of formula II may be converted into acid addition salt forms in conventional manner and vice versa. Suitable acids for salt formation include fumaric acid, malonic acid, and maleic acid.

Compounds of formula II$_p$ may be obtained by reducing a compound of formula III$_p$

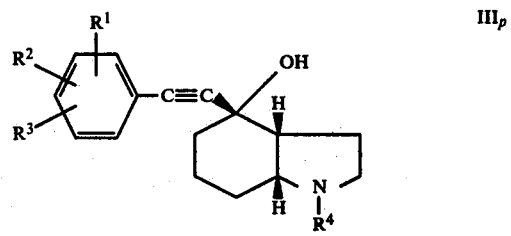

wherein R$^1$, R$^2$, R$^3$ and R$^4$ are as defined above, in conventional manner, e.g. by hydrogenolysis in the presence of a Lindlar catalyst, ie palladium (about 5 to 15%, eg 10%) on barium sulfate or calcium carbonate poisoned (partially inactivated) with quinoline or lead acetate. The particular amount of catalyst employed is not critical; conventional practice being exercised.

Compounds of formula III$_p$ may be obtained by condensing a compound of formula IV$_p$

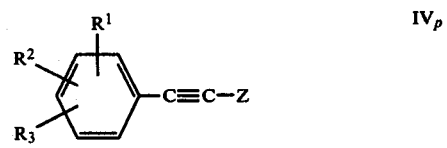

wherein
R$^1$, R$^2$ and R$^3$ are as defined above, and
Z is Li, MgCl, MgBr or MgI, with a compound of formula V$_p$

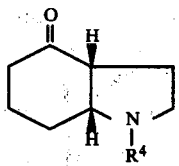

wherein R[4] is as defined above, according to known techniques.

Insofar as the production of any particular starting material involved in the above-presented preparation of Compound II is not described, this is known or may be prepared in conventional manner.

Other reagents and reactants described herein, e.g., compounds III, IV, V, and VI are known and obtainable by known means, or where not known, may be obtained by adaptation of methods reported in the literature for the preparation of known analogs; many such compounds being commercially available.

The final products and intermediate compounds described herein may be recovered and refined, where such is desired, by conventional means, such as by crystallization, distillation or chromatographic techniques such as column or thin layer chromatography.

STATEMENT OF UTILITY

The compounds of formula I of this invention are useful as pharmaceutical agents in animals. In particular, the compounds of the formula I are useful in controlling the cholesterol ester content of mammalian arterial walls and are therefore particularly indicated for use as antiatherosclerotic agents, ie. agents useful in the prophylactic treatment of atherosclerosis and in the controlling of atherosclerotic conditions due to cholesterol ester accumulation in the arterial walls. Such ability of the compounds of the formula I is indicated by known test procedures in which the total cholesterol ester content of cultured cells is shown to be reduced by a test compound, as compared to untreated cells, and carried out, for example, by the following procedures:

(A) Cell culture

Rhesus monkey smooth muscle cells (from the arterial, eg. aorta, wall) obtained by the method of K. Fisher-Dzoga et al (Experimental and Molecular Pathology 18, 162–176 (1973)) are routinely grown in 75 cm² tissue culture flasks using Minimum Essential Medium (Eagle) supplemented with 10% fetal bovine serum. For testing a 75 cm² flask with a near confluent cell growth is selected. The cells are removed from the flask surface by mild enzymatic treatment with pronase. After centrifugation and decanting the enzyme solution, the cell pellet is resuspended in an appropriate volume of media for seeding the desired number of 60 mm tissue culture dishes. Five (5) ml of the diluted cell suspension are pipetted into each dish. After seeding, the dishes are labelled with the cell type, date and flask number of origin and incubated at 37° C. in approximately 5% $CO_2$ atmosphere in a high humidity incubator. When the cultures are confluent, the actual drug testing is begun. Test compounds are routinely solubilized in 100% ethanol. An equivalent amount of ethanol is added to control groups as well. The tissue culture dishes are randomly divided into groups. To one group, hyperlipemic rabbit serum (HRS) is added at 5% by volume (control). To the remaining groups, 5% HRS and 1 mg per 100 ml of media of the test compound are added. The dishes are returned to the incubator for an additional 24 hours. All operations through to the final incubation are performed using sterile technique in a laminar flow hood. After the incubation period, the dishes are microscopically observed with the Zeiss Axiomat with phase contrast optics and the conditions of the cultures are recorded; especially in regard to the size, number and configuration of cytoplasmic inclusions and to cellular morphology. The media is removed from the cultures and 0.9% sodium chloride solution is added. The cells are removed from the flasks with the aid of a rubber policeman and transferred to a conical graduated centrifuge tube. The cells are washed three times by suspending in an isotonic salt solution, centrifuging at 800×g for 10 minutes and aspirating the supernatant fluid.

(B) Cell extraction procedure

An appropriate volume of isopropyl alcohol (about 1 ml/mg protein) is then added to the cell pellet and the sample sonicated with a micro probe (140×3 mm) for 10 seconds with a "LO" setting of 50 on a Bronwell Biosonik IV. After centrifugation for 15 minutes at 800×g, the clear supernatant is decanted and an aliquot taken for cholesterol analysis.

The residue is dissolved in 0.1 N sodium hydroxide and an aliquot taken for protein determination by the method of Lowry, et al. (J. Biol. Chem. 193, 265; 1951).

(C) Assay

Free cholesterol: The isopropyl alcoholic solutions of standards, samples and blank (isopropyl alcohol alone) are treated in a similar manner. An aliquot of 0.4 ml of free reagent (Reagent A, Table 1 below) is added to a 10×75 mm disposable glass test tube to which 20 μl of the isopropyl alcoholic solution is added and mixed. After standing at room temperature for approximately 5 minutes, 0.8 ml of 0.5 N sodium hydroxide (Reagent C, Table 1) is added and mixed. The fluorescence is measured with an Aminco-Bowman spectrophotofluorometer with an excitation wavelength of 325 nm and emission wavelength of 415 nm. A 1 cm light path cuvette is used with a xenon lamp, an IP28 photomultiplier tube and 2 mm slits.

Total cholesterol: The same procedure described above for free cholesterol is followed for total cholesterol except that the total reagent (Reagent B, Table 1) is used instead of the free reagent and the samples are incubated for 20 minutes at 37° C. before the addition of the 0.5 N sodium hydroxide solution (Reagent C, Table 1).

Alternatively, the assay for cholesterol, ie Step C (above) obtained from Steps A and B, may be carried out by the method of Ishikawa et al (J. Lipid Res. 15, 286; 1974).

The amount of cholesterol ester is found by subtracting the amount of free cholesterol from the total cholesterol content of the cells determined by the assay. A finding of a lower amount of cholesterol ester in the group of cells to which test compound was added, as compared to the control group (untreated) shows that the test compound is active in reducing the cholesterol ester in the cells.

Table 1
Composition of Reagents for Cholesterol Determination

A. Free Cholesterol Reagent

| | | |
|---|---|---|
| Sodium phosphate buffer pH 7.0 | .05 | M |
| Cholesterol oxidase | .08 | U/ml |
| Horseradish peroxidase | 30. | U/ml |
| p-Hydroxyphenylacetic acid | .15 | mg/ml |

B. Total Cholesterol Reagent

| | | |
|---|---|---|
| Sodium phosphate buffer pH 7.0 | .05 | M |
| Cholesterol ester hydrolase | .08 | U/ml |
| Cholesterol oxidase | .08 | U/ml |
| Horseradish peroxidase | 30. | U/ml |
| Sodium taurocholate | 5. | mM |
| Carbowax-6000 | .17 | mM |
| p-Hydroxyphenylacetic acid | .15 | mg/ml |

C. Sodium Hydroxide Solution .5N

Following the above-described test method, comparative test results were carried out and are reported in Table 2 below, in which monkey aortic smooth muscle cells were originally obtained from Dr. K. Fisher-Dzoga: Univ. of Chicago, the text compound (Compound A) is 1-(1-oxo-9,12-cis,cis-octadecadienyl)-(3aRS, 4RS, 7aRS)-4-(Z)-(3,4-dimethoxy)-styryl-hexahydro-4-indolinol; (product of Example 1)

Table 2
Comparative Test

| Compound | Protein mg/culture | Cholesterol (pg/mg cell protein) | | | | Per cent from control |
|---|---|---|---|---|---|---|
| | | Total | Free | Ester Amount | mean | |
| None (Control) | 0.528 | 54.1 | 36.0 | 18.1 | 19.3 | — |
| None | 0.468 | 61.0 | 40.6 | 20.4 | | |
| A | 0.450 | 47.9 | 41.3 | 6.6 | 3.6 | 81.0* ↓ |
| A | 0.382 | 45.4 | 44.8 | 0.6 | | |

As is the present understanding in the art, controlling the total cholesterol content of an arterial wall by inhibiting the accumulation thereof by reducing the cholesterol ester content thereof, advantageously inhibits the formation of plaques in the arterial wall.

When the compounds are employed for the above utility, they may be combined with one or more pharmaceutically acceptable carriers, e.g., solvents, diluents and the like, and may be administered orally in such forms as tablets, capsules, dispersible powders, granules, suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The antiatherosclerotic effective dosage of active ingredient employed for the reduction of cholesterol ester content in the arterial walls of a mammal may vary depending on the particular compound employed, the mode of administration and the severity of the condition being treated. However, in general, satisfactory results are obtained when the compounds of formula I are administered at a daily dosage of from about 2 milligrams to about 500 milligrams per kilogram of animal body weight, preferably given in divided doses two to four times a day, or in sustained release form. For most large mammals, the total daily dosage is from about 100 milligrams to about 5,000 milligrams preferably from about 100 milligrams to 2,000 milligrams. Dosage forms suitable for internal use comprise from about 25 to 2,500 milligrams of the active compound in intimate admixture with a solid or liquid pharmaceutically acceptable carrier. Solid carriers include starch, lactose and kaolin, while liquid carriers include sterile water, polyethylene glycols and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants eg vitamin E, ascorbic acid, BHT and BHA.

The preferred pharmaceutical compositions from the stand-point of ease of preparation and administration are solid compositions, particularly tablets and hard-filled or liquid-filled capsules.

A representative formulation for administration orally three times a day prior to feeding in the treatment of atherosclerosis is a gelatin capsule prepared by conventional techniques to contain the following

| Ingredient | Weight (in Mg.) |
|---|---|
| 1-(1-oxo-9-cis-octadecenyl)-(3aRS, 4RS, 7aRS)-4-(Z)-(3,4-dimethoxy)-styryl-hexahydro-4-indolinol | 300 |
| corn oil | 500 |

The following examples relate to the practice of the invention. All temperatures are centigrade (uncorrected) and room temperature is 20° to 30° C., unless indicated otherwise.

Examples, below, are presented as illustrative of the preparation of intermediates II, ie Examples A1 to Ad.

EXAMPLE A1

(3aRS,4RS,7aRS)-4-(3,4-dimethoxy-(Z)-styryl)-hexahydro-4-indolinol*

*may also be called (3aRS, 4RS, 7aRS)-4-(Z)-(3,4-dimethoxy)-styryl-hexahydro-4-indolinol.

30 g of (3aRS,4RS,7aRS)-4-(Z)-(3,4-dimethoxy)-styryl-hexahydro-4-hydroxy-1-indoline carboxylic acid ethyl ester are heated in 145 ml methanol, 145 ml dimethyl sulphoxide and 300 ml 30% (w/v) NaOH for 16 hours at 95°. The mixture is poured into ice water and the aqueous phase extracted with ether. The ether phase is extracted with 2 N tartaric acid solution. The acidic extract is made alkaline and continuously extracted with methylene chloride. The methylene chloride extract is dried over magnesium sulphate, filtered and concentrated. The residue (the title compound in free base form) is converted into the hydrogen maleate of the title compound; M.Pt. 219°–220°.

The starting material is obtained as follows:

(a) A solution of 25.8 g cis-perhydro-4-oxo-1-indoline carboxylic acid ethyl ester in 200 ml absolute tetrahydrofuran is added at −30° to −40° to 1 mole of lithium 3,4-dimethoxyphenylacetylide in tetrahydrofuran (formed from 2 moles 2 molar butyl lithium in hexane and 1 mole 1-(2,2-dibromovinyl)-3,4-dimethoxybenzene in 300 ml benzene at −70°). The mixture is stirred overnight. 100 ml concentrated ammonium chloride solution is added with ice cooling. The organic phase is worked up to give (3aRS,4RS,7aRS)-4-(3,4-dimethoxy)- phenylethinyl)-hexahydro-4-hydroxy-1-indoline carboxylic acid ethyl ester; M.Pt. 153°–155° (from ether).

(b) 23.4 g (3aRS,4RS,7aRS)-(3,4-dimethoxy)-phenylethinyl-hexahydro-4-hydroxy-1-indoline carboxylic acid ethyl ester in 370 ml benzene is hydrogenated in the presence of 1.17 g of 10% palladium on barium sulfate poisoned with 3 ml of 5% (v/v) quinoline solution in benzene. After filtration (3aRS,4RS,7aRS)-4-(3,4-dimethoxy)-(Z)-styryl)-hexahydro-4-hydroxy-1-indoline carboxylic acid ethyl ester is obtained as an oil after working up.

In analogous manner to that described in Example A1 from the appropriate compounds of formulae $II_p$ and $III_p$ wherein $R^4$ is ethoxycarbonyl, the following compounds of formula II are obtained, wherein

| EXAMPLE No. | $R^1$ | $R^2$ | $R^3$ | M.Pt. |
|---|---|---|---|---|
| A2 | 4-CH₃ | H | H | 88°–90°(1) |
|   |   |   |   | 108°–110°(2) |
| A3 | 4-CH₃O | H | H | 183°–185°(3)(4) |
| A4 | 4-Cl | H | H | 222°–224°(4)(5) |
| A5 | 2-Cl | H | H | 191°–193°(6) |
| A6 | H | H | H | 222°–223°(5)(7) |
| A7 | 2-Cl | 6-Cl | H | 159°–162°(1) |
| A8 | 3-CF₃ | H | H | 202°–203°(5) |
| A9 | 3-CH₃O | H | H | 154°–156°(3) |
| A10 | 4-F | H | H | 210°–212°(5) |
| A11 | 3-Cl | 4-Cl | H | 206°–208°(5) |
| A12 | 3-CH₃O | 4-CH₄O | 5-CH₃O | 112°–114°(1) |
| A13 | 2,3-CH=CH—CH=CH— |   | H | 115°–117°(1) |
| A14 | 3,4-O—CH₂—O— |   | H | 154°–156°(3) |
| A15 | 3-CH₃ | 4-CH₃ | H |   |

(1) free base
(2) hydrogen malonate
(3) bis[base]malonate
(4) decomposition
(5) bis[base]fumarate
(6) hydrogen fumarate
(7) M.Pt. of corresponding formula $III_p$ compound 104°–105°

In analogous manner the following compounds of formula II may also be prepared:

|   | $R^1$ | $R^2$ | $R^3$ |
|---|---|---|---|
| (A$_a$) | 2,3-O—CH₂—CH₂— |   | 4-F |
| (A$_b$) | 2,3-CH₂—CH₂—O— |   | 4-C₂H₅ |
| (A$_c$) | 3,4-(CH₂)₄— |   | 5-CF₃ |
| (A$_d$) | 3,4-CH=CH—CH=CH— |   | 2-C₂H₅O |

The following Examples are illustrative of the invention:

EXAMPLE 1

Preparation of 1-(1-oxo-9,12-cis,cis-octadecadienyl)-(3aRS, 4RS, 7aRS)-4-(Z)-(3,4-dimethoxy)-styryl-hexahydro-4-indolinol

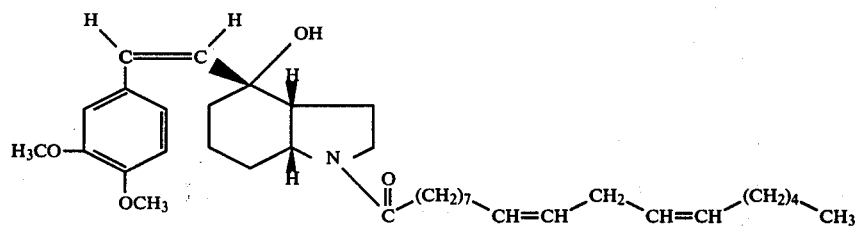

To a cooled solution of 1.5 g linoleic acid in 100 ml of methylene chloride at −30° is added 0.56 g triethylamine and thereafter 0.6 g ethylchloroformate. The reaction mixture is allowed to warm to room temperature and then stirred for 2 hours. Thereafter is added 0.56 g triethylamine followed by 2.0 g of (3aRS, 4RS, 7aRS)-4-(Z)-(3,4-dimethoxy)-styryl-hexahydro-4-indolinol maleate, and the mixture stirred at room temperature for 16 hours. The reaction mixture is then extracted several times with 2 N aqueous sodium hydroxide, washed with saturated aq. sodium chloride solution, and the organic phase dried over anh. sodium sulfate, filtered and the filtrate evaporated i.v. to dryness. The residue is then filtered over silica gel using chloroform as the eluant to obtain the title product in solvent, which is then evaporated to yield the title product as an oil.

EXAMPLE 2

Repeating the procedure of Example 1, but using in place of the linoleic acid used therein, an approximately equivalent amount of:
(a) oleic acid;
(b) linolenic acid;
(c) palmitoleic acid; or
(d) arachidonic acid;
there is accordingly obtained:
(a) 1-(1-oxo-9-cis-octadecenyl)-(3aRS, 4RS, 7aRS)-4-(Z)-(3,4-dimethoxy)-styryl-hexahydro-4-indolinol; and the analogous
(b) 1-(1-oxo-9,12,15-cis,cis,cis-octadecatrienyl);
(c) 1-(1-oxo-9-cis-hexadecenyl); and
(d) 1-(1-oxo-5,8,11,14-cis,cis,cis,cis-eicosatetraenyl)-amides of the hexahydroindolinol.

EXAMPLE 3

Repeating the procedures of Examples 1 or 2a, but using as compound II in place of the particular styryl hexahydroindolinol compound (II) used therein, the following analogs (in the free or an acid addition salt form thereof):
(a) 4-methoxy;
(b) 4-methyl;
(c) 4-chloro;
(d) 2-chloro;
(e) unsubstituted (ie $R^1=R^2=R^3=H$);
(f) 2,6-dichloro;
(g) 3-trifluoromethyl;
(h) 3-methoxy;
(i) 3,4-dichloro-
(j) 3,4,5-trimethoxy-, or
(k) 3,4-dioxymethylene;
the corresponding compounds I' are similarly obtained.

EXAMPLE 4

Repeating the procedures of Examples 1 and 2a, but using as compound II, in place of the particular styryl-hexahydroindolinol used therein an approximately equivalent amount of (3aRS, 4RS, 7aRS)-4-(Z)-[2-(α-naphthyl)]-vinylhexahydro-4-indolinol, the corresponding compounds I' are similarly obtained.

EXAMPLE 5

Preparation of 1-[1-oxo-2-cis-octylcyclopropanoctyl] (3aRS, 4RS, 7aRS)-4-(Z)-(3,4-dimethoxy)-styryl-hexahydro-4-indolinol

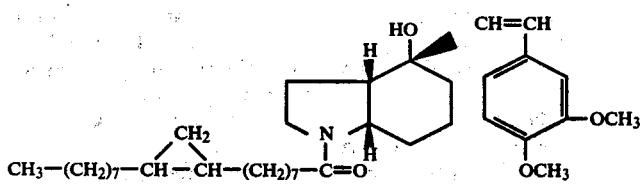

To a cooled solution of 1.64 g of dihydrosterculic acid in 100 ml of methylene chloride at −30° is added 0.56 g triethylamine and thereafter 0.6 g ethylchloroformate. The reaction mixture is allowed to warm to room temperature and then stirred for 2 hours. Thereafter is added 0.56 g triethylamine followed by 2.0 g of (3aRS, 4RS, 7aRS)-4-(Z)-(3,4-dimethoxy)-styryl-hexahydro-4-indolinol maleate, and the mixture stirred at room temperature for 16 hours. The reaction mixture is then extracted several times with 2 N aqueous sodium hydroxide, washed with saturated aq. sodium chloride solution, and the organic phase dried over anh. sodium sulfate, filtered and the filtrate evaporated i.v. to dryness. The residue is then filtered over silica gel using chloroform as the eluant to obtain the title product in solvent, which is then evaporated to yield the title product.

EXAMPLE 6

1-{1-oxo-cis,cis-2-[(2-pentylcyclopropyl)-methyl]-cyclopropanoctyl}-(3aRS, 4RS, 7aRS)-4-Z-(3,4-dimethoxy)-styryl-hexahydro-4-indolinol

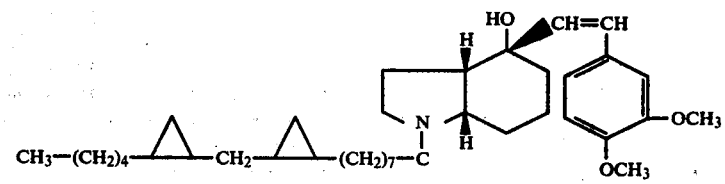

Repeating the procedure of Example 1, but using in place of the dihydrosterculic acid used therein, an approximately equivalent amount of cis,cis-2-[(2-pentylcyclopropyl)-methyl]-cyclopropanoctanoic acid there is accordingly obtained the title product.

EXAMPLE 7

Repeating the procedures of Examples 5 or 6, but using as compound II in place of the styryl hexahydro-4-indolinol compound (II) used therein, the following analogs (in the free or an acid addition salt form thereof):
(a) 4-methoxy;
(b) 4-methyl;
(c) 4-chloro;
(d) 2-chloro;
(e) unsubstituted (ie $R^1=R^2=R^3=H$);
(f) 2,6-dichloro;
(g) 3-trifluoromethyl;
(h) 3-methoxy;
(i) 3,4-dichloro-
(j) 3,4,5-trimethoxy-, or
(k) 3,4-dioxymethylene;
the corresponding compounds I" are similarly obtained.

EXAMPLE 8

Repeating the procedures of Examples 5 and 6, but using as compound II, in place of the particular styryl-hexahydroindolinol used therein, an approximately equivalent amount (3aRS, 4RS, 7aRS)-4-(Z)-[2-(α-naphthyl)]-vinyl-hexahydro-4-indolinol, there is accordingly obtained the corresponding compounds I".

What is claimed is:
1. A compound of the formula:

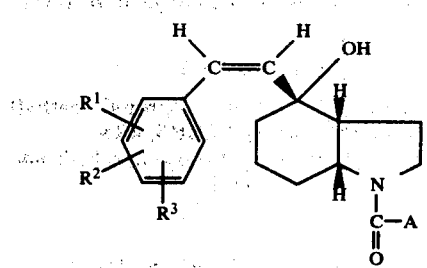

wherein
R$^1$ and R$^2$ are, independently, hydrogen, fluorine, chlorine, trifluoromethyl, alkyl of 1 to 4 carbon atoms, or alkoxy of 1 to 4 carbon atoms, and
R$^3$ is hydrogen, or alkoxy of 1 to 4 carbon atoms, with the proviso that when R$^1$ and R$^2$ are both other than hydrogen and R$^3$ is alkoxy then at least one of R$^1$ and R$^2$ is alkoxy, or
R$^1$ and R$^2$ are bound to adjacent ring carbon atoms and are together —(CH$_2$)$_q$—, wherein q is 3 or 4, —CH=CH—CH=CH—, or —O—CH$_2$—X—, wherein X is —O— or —CH$_2$—, and
R$^3$ is hydrogen, fluorine, chlorine, trifluoromethyl, alkyl of 1 to 4 carbon atoms, or alkoxy of 1 to 4 carbon atoms; and A is either of type A', wherein A is the residue of an unsaturated long-chain fatty acid minus the carboxylic portion, said acid having from 8 to 24 carbon atoms and having from 1 to 4 ethylenically unsaturated positions; or A is of type A", wherein A is a saturated hydrocarbon radical having from 1 to 4 cyclopropanyl groups of the formula

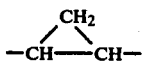

said A having from 7 to 23 carbon atoms plus one carbon atom for each cyclopropanyl group present.

2. A compound of claim 1 in which A is of type A'.
3. A compound of claim 2 in which A is of either the types (A1) having the structure:

or (A2) having the structure

in which
f is a whole integer of from 1 to 10,
g is a whole integer of from 1 to 4, and
h is a whole integer of from 3 to 9;
n is a whole integer of from 1 to 4,
m is a whole integer of from 2 to 4,
and p is a whole integer of from 1 to 7.

4. A compound of claim 3 in which A' is of type (A1).
5. A compound of claim 4 in which A' is the residue of oleic acid.
6. A compound of claim 4 in which A' is the residue of palmitoleic acid.
7. A compound of claim 3 in which A' is of type (A2).
8. A compound of claim 7 in which A' is the residue of linoleic acid.
9. A compound of claim 7 in which A' is the residue of linolenic acid.
10. A compound of claim 2 in which each unsaturated position of A is in the cis-type isomeric form.
11. The compound of claim 5 which is 1-(1-oxo-9-cis-octadecenyl)-(3aRS, 4RS, 7aRS)-4-(Z)-(3,4-dimethoxy)-styryl-hexahydro-4-indolinol;
12. The compound of claim 8 which is 1-(1-oxo-9,12-cis,cis-octadecadienyl)-(3aRS, 4RS, 7aRS)-4-(Z)-(3,4-dimethoxy)-styryl-hexahydro-4-indolinol.
13. A compound of claim 1 in which R$^1$ is a hydrogen atom, R$^2$ is 3-methoxy and R$^3$ is 4-methoxy.
14. A compound of claim 1 in which A is of type A".
15. A compound of claim 14 wherein A" is a cyclopropanyl-bearing hydrocarbon radical of the formula:

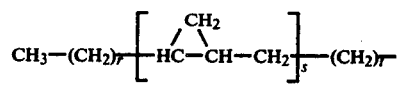

wherein r is a whole integer of from 1 to 15; s is 1 or 2; and t is a whole integer of from 1 to 13, provided that when s is 1, then r+t is from 3 to 19, and when s is 2 then r+t is from 2 to 16.

16. A compound of claim 15 in which s is 1.
17. A compound of claim 15 in which s is 2.
18. A compound of claim 16 in which r is 7 and t is 6.
19. A compound of claim 17 in which r is 4 and t is 6.
20. A compound of claim 15 in which the hydrogen atoms of each cyclopropanyl group are in the cis configuration.
21. A method of reducing the cholesterol ester content of an arterial wall, in a mammal in need of such treatment, comprising administering a cholesterol ester-reducing amount of a compound of claim 1 to said mammal.
22. A method of claim 21 in which A of the compound is of type A'.
23. A method of claim 21 in which A of the compound is of type A".
24. A method of claim 22 in which the compound is 1-(1-oxo-9-cis-octadecenyl)-(3aRS, 4RS, 7aRS)-4-(Z)-(3,4-dimethoxy)-styryl-hexahydro-4-indolinol;
25. A pharmaceutical composition suitable for reducing the cholesterol ester content of an arterial wall of a mammal comprising a cholesterol ester-reducing effective amount of a compound of claim 1 and a non-toxic pharmaceutically-acceptable carrier.
26. A composition of claim 25 in which A of the compound is of type A'.
27. A composition of claim 26 in solid form.
28. A composition of claim 26, in which the compound is present in an amount of from about 25 to 2,500 milligrams.
29. A composition of claim 26 in which the compound is 1-(1-oxo-9-cis-octadecenyl)-(3aRS, 4RS, 7aRS)-4-(Z)-(3,4-dimethoxy)-styryl-hexahydro-4-indolinol;
30. A composition of claim 25 in which A is of type A".
31. A composition of claim 30 in solid form.
32. A composition of claim 30, in which the compound is present in an amount of from about 25 to 2,500 milligrams.

* * * * *